US010213165B2

(12) United States Patent
Eyring

(10) Patent No.: US 10,213,165 B2
(45) Date of Patent: *Feb. 26, 2019

(54) SYSTEMS AND METHODS FOR MEASURING CALORIE INTAKE

(71) Applicant: Vivint, Inc., Provo, UT (US)

(72) Inventor: Matthew J. Eyring, Provo, UT (US)

(73) Assignee: Vivint, Inc., Provo, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/676,697

(22) Filed: Aug. 14, 2017

(65) Prior Publication Data

US 2018/0028126 A1    Feb. 1, 2018

Related U.S. Application Data

(63) Continuation of application No. 14/253,772, filed on Apr. 15, 2014, now Pat. No. 9,730,647.

(51) Int. Cl.
*A61B 5/00* (2006.01)
*G02B 27/01* (2006.01)

(52) U.S. Cl.
CPC .............. *A61B 5/742* (2013.01); *A61B 5/486* (2013.01); *A61B 5/4866* (2013.01); *G02B 27/017* (2013.01); *G02B 2027/014* (2013.01); *G02B 2027/0138* (2013.01); *G02B 2027/0141* (2013.01); *G06K 2209/17* (2013.01)

(58) Field of Classification Search
CPC combination set(s) only.
See application file for complete search history.

(56) References Cited

U.S. PATENT DOCUMENTS

| | | | | |
|---|---|---|---|---|
| 8,905,542 | B2 * | 12/2014 | Howell | G02C 5/001 351/158 |
| 9,730,647 | B2 * | 8/2017 | Eyring | G02B 27/017 |
| 2003/0076983 | A1 * | 4/2003 | Cox | G06F 19/3475 382/110 |
| 2005/0113650 | A1 * | 5/2005 | Pacione | A61B 5/411 600/300 |
| 2010/0111383 | A1 * | 5/2010 | Boushey | G06K 9/00 382/128 |
| 2010/0173269 | A1 * | 7/2010 | Puri | G09B 19/0092 434/127 |
| 2011/0077471 | A1 * | 3/2011 | King | A61B 5/16 600/300 |

(Continued)

OTHER PUBLICATIONS

International Search Report and Written Opinion of the International Searching Authority for PCT/US2015/024833, dated Jun. 29, 2015.

(Continued)

*Primary Examiner* — Tsung-Yin Tsai
(74) *Attorney, Agent, or Firm* — Holland & Hart LLP

(57) ABSTRACT

Systems and methods for measuring calorie input are described. A calorie measure may be maintained. At least one image of a food item may be captured. The at least one image of the food item may be transmitted to a server. A calories consumed value may be received from the server. The calories consumed value may be determined based at least in part on the at least one image of the food item. The calorie measure may be updated based on the received calories consumed value.

20 Claims, 11 Drawing Sheets

(56) References Cited

U.S. PATENT DOCUMENTS

| | | | | |
|---|---|---|---|---|
| 2012/0094258 A1* | 4/2012 | Langheier | ........... | G06F 19/3475 |
| | | | | 434/127 |
| 2012/0135384 A1 | 5/2012 | Nakao | | |
| 2012/0178065 A1* | 7/2012 | Naghavi | ............ | G09B 19/0092 |
| | | | | 434/236 |
| 2013/0095459 A1* | 4/2013 | Tran | ..................... | A61B 5/6816 |
| | | | | 434/247 |
| 2013/0157232 A1* | 6/2013 | Ehrenkranz | ........ | G01G 19/4146 |
| | | | | 434/127 |
| 2013/0335418 A1* | 12/2013 | Kim | ....................... | G06Q 10/00 |
| | | | | 345/424 |
| 2013/0336519 A1 | 12/2013 | Connor | | |
| 2014/0160250 A1* | 6/2014 | Pomerantz | ......... | H04N 5/23229 |
| | | | | 348/47 |
| 2014/0349256 A1* | 11/2014 | Connor | .............. | G09B 19/0092 |
| | | | | 434/127 |
| 2014/0349257 A1* | 11/2014 | Connor | .............. | G09B 19/0092 |
| | | | | 434/127 |
| 2015/0126873 A1* | 5/2015 | Connor | ................ | A61B 5/4866 |
| | | | | 600/475 |
| 2015/0228062 A1* | 8/2015 | Joshi | ...................... | G06Q 50/12 |
| | | | | 382/110 |

OTHER PUBLICATIONS

Jans, I. , "Calorie Counter While Eating With Google Glass", (http://imagine-life-with-google-glass.blogspot.com/2013/06/calorie-counter-while-eating-with.html), Jun. 21, 2013.

* cited by examiner

SYSTEMS AND METHODS FOR MEASURING CALORIE INTAKE

CROSS-REFERENCE TO RELATED APPLICATIONS

The present application is a continuation application of U.S. patent application Ser. No. 14/253,772, titled "Systems and Methods for Measuring Calorie Intake," filed on Apr. 15, 2014. The disclosure of the application listed above is incorporated by reference herein in its entirety.

BACKGROUND

Eating is a necessary part of life. The body needs fuel (e.g., food) to function and operate properly. This need for fuel is often expressed in the hunger urge. The hunger urge drives consumers to eat (e.g., consume calories). However, consumers eat for a variety of reasons other than satisfying their hunger. For example, consumers may eat simply for the purpose of being social. Indeed, eating has become a social activity and food has become deeply intertwined with social interaction. This leads consumers to eat more when they are with others who are eating. Advertising has also led to an increase in the consumption of food. In addition to the many promotional reasons for eating, consumers may also use eating as a coping mechanism for dealing with negative emotion (e.g., stress, depression, etc.). As a result consumers often overeat. Overeating, coupled with lifestyle behaviors that are increasingly sedentary, has led to epidemic numbers of consumers being overweight and/or obese.

These negative trends have resulted in increased attention to becoming health conscience. Approaches for becoming healthy (e.g., maintaining a healthy weight) include increasing the number of calories that are burned (through exercise, for example) and/or limiting the number of calories that are consumed (by calorie tracking, for example). Tracking calories has proven to be a difficult problem. Current calorie trackers require consumers to manually enter all of the calories that they consume. This means that each time the consumer eats they must figure out how many calories they are eating and enter that information into the calorie tracker. Often, the process of manually entering calorie information becomes so tedious that consumers lose interest and stop tracking the calories they consume. In another approach, calories may be tracked by only eating the items that are provided to the consumer as part of a specially prepared diet. While this approach allows for exact tracking of calorie intake, the specially prepared meals take away the spontaneity and many of the social aspects of eating. Furthermore, it is difficult for consumers to limit their eating to the specially prepared meals when they are constantly surrounded with food and/or social settings that include food.

SUMMARY

Systems and methods for measuring calorie input are described. For example, a computer-implemented method for measuring calorie input, is described. A calorie measure may be maintained. At least one image of a food item may be captured. The at least one image of the food item may be transmitted to a server. A calories consumed value may be received from the server. The calories consumed value may be determined based at least in part on the at least one image of the food item. The calorie measure may be updated based on the received calories consumed value.

In some embodiments, the calorie measure may be displayed on a display. In some cases, displaying the calorie measure includes displaying the updated calorie measure. In one example, displaying the calorie measure includes persistently displaying the calorie measure. In some embodiments, the display may be a heads-up display (HUD).

In some embodiments, capturing the at least one image of the food item includes capturing a pre-consumption image of the food item and capturing a post-consumption image. In some cases, an identifier associated with the food time may be received from the server. In one example, the food item may be identified based on the pre-consumption image of the food item. In some cases, portion information for the identified food item may be determined. In one example, the portion information may be determined based at least in part on the pre-consumption image of the food item. In some embodiments, calorie information for the food item may be received from the server. In one example, the calorie information may be based at least in part on the identified food and the determined portion information. In some cases, the calorie information for the food item may be displayed on the display.

In some cases, the calorie information may be transmitted to a device. In some cases, the calorie measure may additionally or alternatively be transmitted to the device. In one example, feedback may be received from the device. The feedback may be based on the transmitted calorie information or the transmitted calorie measure.

In some embodiments, a consumption event summary may be received from the server. In one example, the consumption event summary includes a list of foods consumed, the calories consumed value for each of the items of food in the list of foods, a timestamp associated with a consumption period, and/or a duration of the consumption period.

A computing device for measuring calorie input is also described. The computing device includes a processor and instructions stored in memory. The instructions are executable by the processor to: maintain a calorie measure, capture at least one image of a food item, transmit to a server the at least one image of the food item, receive a calories consumed value from the server wherein the calories consumed value may be determined based at least in part on the at least one image of the food item, and update the calorie measure based on the received calories consumed value.

A computer-program product for measuring calorie input is also described. The computer-program product includes a non-transitory computer-readable medium containing instructions that when executed by a processor cause the processor to: maintain a calorie measure, capture at least one image of a food item, transmit to a server the at least one image of the food item, receive a calories consumed value from the server wherein the calories consumed value may be determined based at least in part on the at least one image of the food item, and update the calorie measure based on the received calories consumed value.

The foregoing has outlined rather broadly the features and technical advantages of examples according to the disclosure in order that the detailed description that follows may be better understood. Additional features and advantages will be described hereinafter. The conception and specific examples disclosed may be readily utilized as a basis for modifying or designing other structures for carrying out the same purposes of the present disclosure. Such equivalent constructions do not depart from the spirit and scope of the appended claims. Features which are believed to be characteristic of the concepts disclosed herein, both as to their organization and method of operation, together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the embodiments may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

Figure 1:
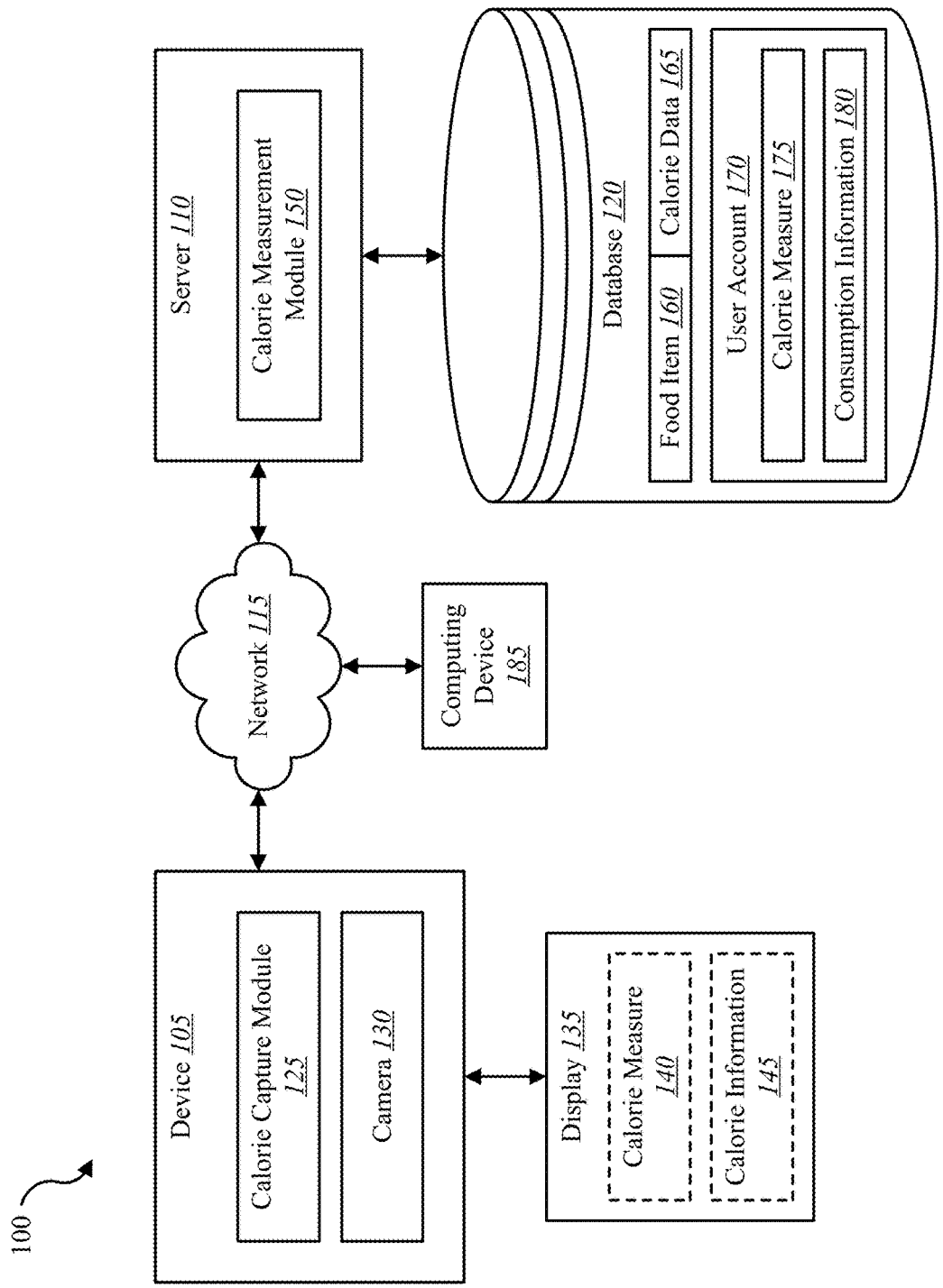
FIG. 1 is a block diagram of an environment in which the present systems and methods may be implemented.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

The systems and methods described herein relate to calorie tracking. More specifically, the systems and methods described herein relate to an automated system for measuring the number of calories that is consumed. In one example, calories consumed value may be determined based on a difference between a pre-consumption image of a food item and a post-consumption image. In some cases, this may allow for calories to be determined and tracked with little or no effort by the user.

FIG. 1 is a block diagram illustrating one embodiment of an environment 100 in which the present systems and methods may be implemented. In some embodiments, the systems and methods described herein may be performed on a device (e.g., device 105). The environment 100 may include a device 105, a server 110, a computing device 185, and/or a network 115 that allows the device 105, server 110, and computing device 185 to communicate with one another. Examples of device 105 include smart wearable devices, mobile devices, smart phones, personal computing devices, computers, servers, etc. Examples of the server 110 and/or the computing device 185 include a personal computing device (e.g., laptop, desktop, etc.), a mobile computing device (e.g., tablet computing device, smartphone, etc.), a server (e.g., enterprise server, cloud server, etc.) and the like.

In some embodiments, the device 105 may include a calorie capture module 125 and a camera 130. The device 105 may include or may be coupled to a display 135. In one example, the device 105 may be a smart wearable device with the display 135 positioned in such a way that it is in the field of vision of the user (e.g., attached to glasses, integrated into one or more lenses of the glasses, integrated into a contact lens, attached to a hat or visor, projected in a heads-up display, etc.). In some embodiments that display 135 may display a calorie measure 140 that indicates how many calories the user has consumed over a given period of time (e.g., a day). Additionally or alternatively, the display 135 may display calorie information about food that the user is contemplating eating (e.g., that is in the user's field of view). In some embodiments, the camera 130 may capture one or more images that correspond with the user's field of view. In some examples, this may allow for automatic, real time updates to the calorie measure 140 and/or the calorie information 145.

In some embodiments, the calorie capture module 125 may keep track of and display the calorie measure 140. In this way the user may easily view how many calories they have consumed. In some embodiments, the calorie capture module 125 may use the camera 130 to capture a pre-consumption image of a food item. For example, the pre-consumption image may depict a brownie that the user has (e.g., on their fork, in their hand, on their plate, etc.). In one example, the calorie capture module 125 may transmit at least a portion of the pre-consumption image to a calorie measurement module 150 included on the server 110. In one example, the calorie measurement module 150 may use image analysis techniques to identify the food item 160 (brownie, in this example). In another example, the calorie measurement module 150 may allow a human analyst to access the pre-consumption image and identify the food item 160. In one example, the calorie measurement module 150 may use a database 120 to determine the calorie data 165 associated with the food item 160. In some cases, the calorie data 165 may be adjusted to reflect the actual composition of the food item 160 (e.g., thickness, density, etc.). In one example, the calorie measurement module 150 may determine an amount (e.g., portion size) of the food item. The calorie measurement module 150 may determine the calorie information 145 for the food item based on the identified food item 160 and the determined amount of the food item 160. In some cases, the calorie capture module 125 may receive calorie information 145 associated with the food item.

In some cases, displaying the calorie information 145 to the user may help inform the user so that they can make informed choices regarding the food item (whether to eat, how much of a portion to eat, etc., for example). When the display 135 is located within the field of view of the user, the user may have easy access to the calorie information 145 without any additional action. In some embodiments, the calorie capture module 125 may capture one or more additional images of the food item (or lack thereof, for example). In one example, the calorie measurement module 150 may determine an updated calorie measure based on a difference between the amount of the food item in the pre-consumption image and the subsequent image. In some cases, the calorie capture module 125 may dynamically update the calorie measure 140 based on information from the calorie measurement module 150. In the case that the subsequent image is a post-consumption image, the calorie measurement module 150 may determine the total number of calories consumed as a result of eating the food item (brownie, for example). The total number of calories consumed may depend on the amount (e.g., portion) of the food item that the user consumed. The calorie measurement module 150 may communicate information with the calorie capture module 125 (via the network 115, for example) and the calorie capture module 125 may update the calorie measure 140 accordingly.

In one example, the calorie capture module 125 may sync the user's calorie measure and consumption information with a cloud service. For example, the calorie measurement module 150 may maintain a user account 170 for the user in the database 125. In one example, the user account 170 may store the calorie measure 175 for the user and consumption information 180 for the user. In one example, the calorie measure 175 may be tied to the calorie measure 140 that is displayed on the display 135. In one example, the consumption information 180 may correspond to the calories consumed during a given time period (e.g., a meal, breakfast, lunch, dinner, etc.). In some cases, the user account 170 may track the consumption behaviors of the user. For example, the user account 170 may log consumption times, the specific food eaten at the specific times, and may analyze the data to identify trends or habits. In one example, the calorie capture module 125 may display suggestions or warnings (not shown) to the user to help the user to improve their consumption behaviors.

In some cases, the systems and methods described herein may enable for automatic and dynamic calorie tracking (without interaction from the user, for example). Additionally, the systems and methods described herein may enable instant feedback and instantaneous calorie monitoring (within the field of view of the user, for example).

Figure 2:
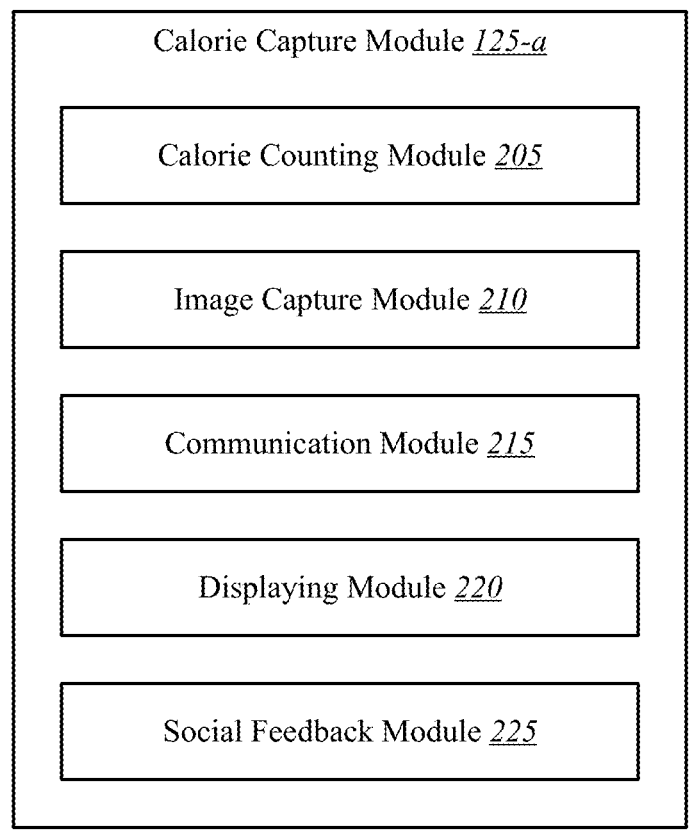
FIG. 2, is a block diagram illustrating one example of a calorie capture module.

FIG. 2, is a block diagram 200 illustrating one example of a calorie capture module 125-*a*. The calorie capture module 125-*a* may be one example of the calorie capture module 125 illustrated in FIG. 1. In one example, the calorie capture module 125-*a* may include a calorie counting module 205, an image capture module 210, a communications module 215, a displaying module 220, and/or a social feedback module 225.

In some embodiments, the calorie counting module 205 may maintain a counter of calories consumed. For example, the calorie counting module 205 may track the number of calories consumed in a given time period (e.g., a meal, a day, etc.). For instance, the calorie counting module 205 may track the number of calories consumed (e.g., 1500) and/or the number of calories remaining (e.g., 500) before the desired calorie target (e.g., 2000) is reached. Since the desired calorie target may be unique for each individual and their desired goals, the calorie counting module 205 may enable a user to select a desired goal. In some cases, the calorie counting module 205 may sync the calorie measure (e.g., number of calories consumed) with a cloud based service.

In some embodiments, the image capture module 210 may use the camera 130 to capture multiple images of the user's field of view. In some cases, the image capture module 210 may use image processing and object recognition tools to identify whether an image includes a food item (and whether the user is likely to eat the food item, for example). In other cases, the image capture module 210 may capture images at a periodic interval (allowing for post analysis and processing, for example). In some cases, the image capture module 210 may capture a pre-consumption image (e.g., image of a food item prior to consumption) and a post-consumption image (e.g., image of leftover food item or absence of the food item after consumption). In some cases, the image capture module 210 may utilize the communication module 215 to transmit the one or more captured images to a calorie measurement module (e.g., calorie measurement module 150).

In some embodiments, the communications module 215 may facilitate communications with other devices. For example, the communications module 215 may enable the device 105 to transmit and/or receive information (e.g., images, calorie measure, consumption information, calorie information, etc.). For example, the communication module 215 may facilitate communications between the calorie capture module 125 and the calorie measurement module 150.

In some embodiments, the display module 220 uses the display 130 to display various information to the user. For example, the display module 220 may format and structure information (e.g., calorie measure 140, calorie information 145, and/or other information) on the display 130.

In some embodiments, the social feedback module 225 may share information to one or more users in a social network and receive information from one or more users in the social network. In some cases, the social feedback module 225 may use the social feedback to promote good consumption habits (user enjoyed the delicious taste of a brownie while staying below his calorie consumption goals', for example) and/or to receive good consumption promoting feedback from others ('way to go user!', for example). In some cases, this may allow for gamification of the consumption experience, while promoting good consumption habits. In other cases, the social feedback module 225 may help the user to hold themselves accountable to their goals ('user has just met his desired calorie target, encourage the user to be successful and not eat any more', for example). In some cases, the social feedback module 225 may use the communication module 215 to communicate with one or more users of a social network.

Figure 3:
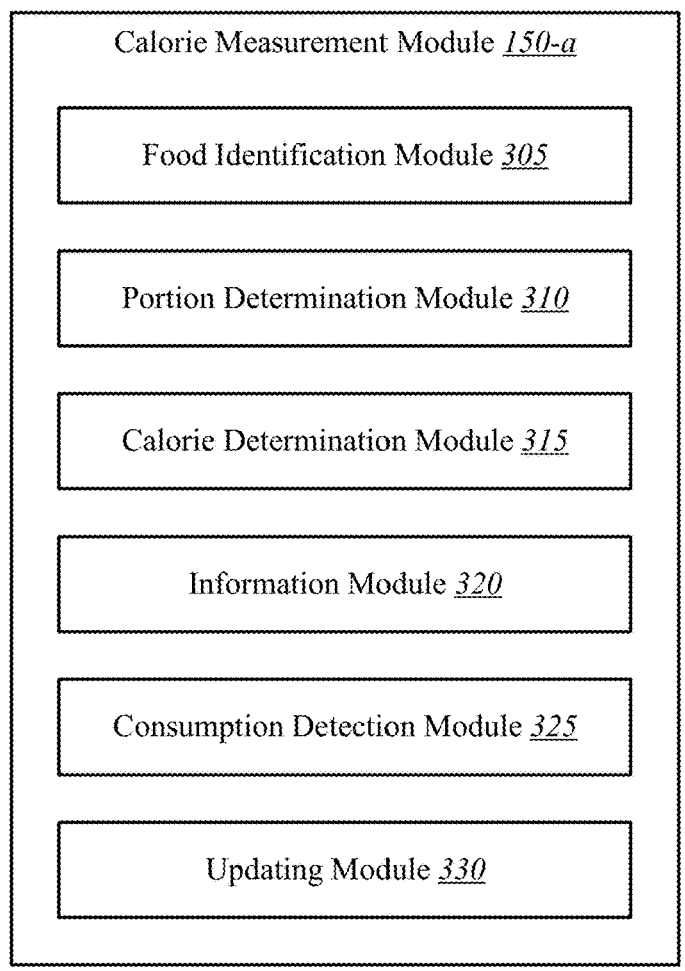
FIG. 3 is a block diagram illustrating one example of a calorie measurement module.

FIG. 3 is a block diagram 300 illustrating one example of a calorie measurement module 150-*a*. The calorie measurement module 150-*a* may be one example of the calorie measurement module 150 illustrated in FIG. 1. In one example, the calorie measurement module 150-*a* may include a food identification module 305, a portion determination module 310, a calorie determination module 315, an information module 320, a consumption detection module 325, and/or an updating module 330.

In some embodiments, the food identification module 305 may analyze an image of a food item to identify the food item. In one example, the food identification module 305 may use image processing and object identification algorithms to automatically detect the size, color, shape, texture, and position of the food item. In some cases, the food identification module 305 may use this information to automatically identify the food item. For example, the food identification module 305 may distinguish an apple from an orange based on the skin texture, reflectivity, transparency, etc. In another example, the food identification module 305 may provide the image (e.g., pre-consumption image) to a human analyst for identification of the food item. In one example, the human analyst may use a disparate computing device to analyze the image of the food item.

In some embodiments, the portion determination module 310 may determine portion information based on the amount (e.g., quantity) of the food item. In some cases, the amount of the food item may be determined based on physical dimensions (e.g., length×width×height) of the food item. In some cases, the portion determination module may determine portion information based on a standard portion size. In some cases, calorie data for the food item may be based on the standard portion size.

In some embodiments, the calorie determination module 315 may determine the calorie information for a food item based on the identified food type and the determined portion size. For example, the calorie determination module 315 may use the determined portion size to scale the standard portion size calorie numbers to the portion size of the food item. For example, if the food identification module 305 identifies a food item as pizza and the portion determination module 310 determines that the amount of the pizza is equivalent to two slices, then the calorie determination module 315 may scale the calorie information for a standard slice of pizza (311 calories, for example) by the portion size of two slices to determine that the food item has twice the calories of a standard slice of pizza (622 calories, for example). In one example, a database of standard portion sizes and the calorie content of standard portion sizes may be maintained in a database (e.g., database 120). In some cases, the calorie determination module 315 may determine the calorie information for the food item for each image of the food item that is received.

In some embodiments, the information module 320 may provide information to the calorie capture module 125. For example, the information module 320 may provide information such as the identified type of the food item, portion size of the food item, and/or calorie information for the food item. Additionally or alternatively, the information module 320 may provide information such as goal information, warnings, trend information, encouragement information, historical information, etc. In some cases, the information module 320 may transmit the determined information to the calorie capture module 125-*a*.

In some embodiments, the consumption detection module 325 may determine an amount of calories consumed based on the difference between the calorie information of a food item in a first image and the calorie information of the food item in a second image (the difference corresponding to the value of calories consumed by the consumer, for example). For instance, in the case that the first image included a 800 calorie burrito and the burrito was half eaten in the second image, then the consumption detection module 325 may determine that the consumer had consumed 400 calories. In one example, the updating module 330 may update the calorie measure 175 and/or consumption information 180 based on the detected consumption. In one example, the updating module 330 may transmit the determined calories consumed value, updated calorie measure 175, and/or updated consumption information to the calorie capture module 125-*a*. In some cases, frequent updates may allow may allow for near or instant updates to the calorie measure 140 and/or calorie information 145.

Figure 4:
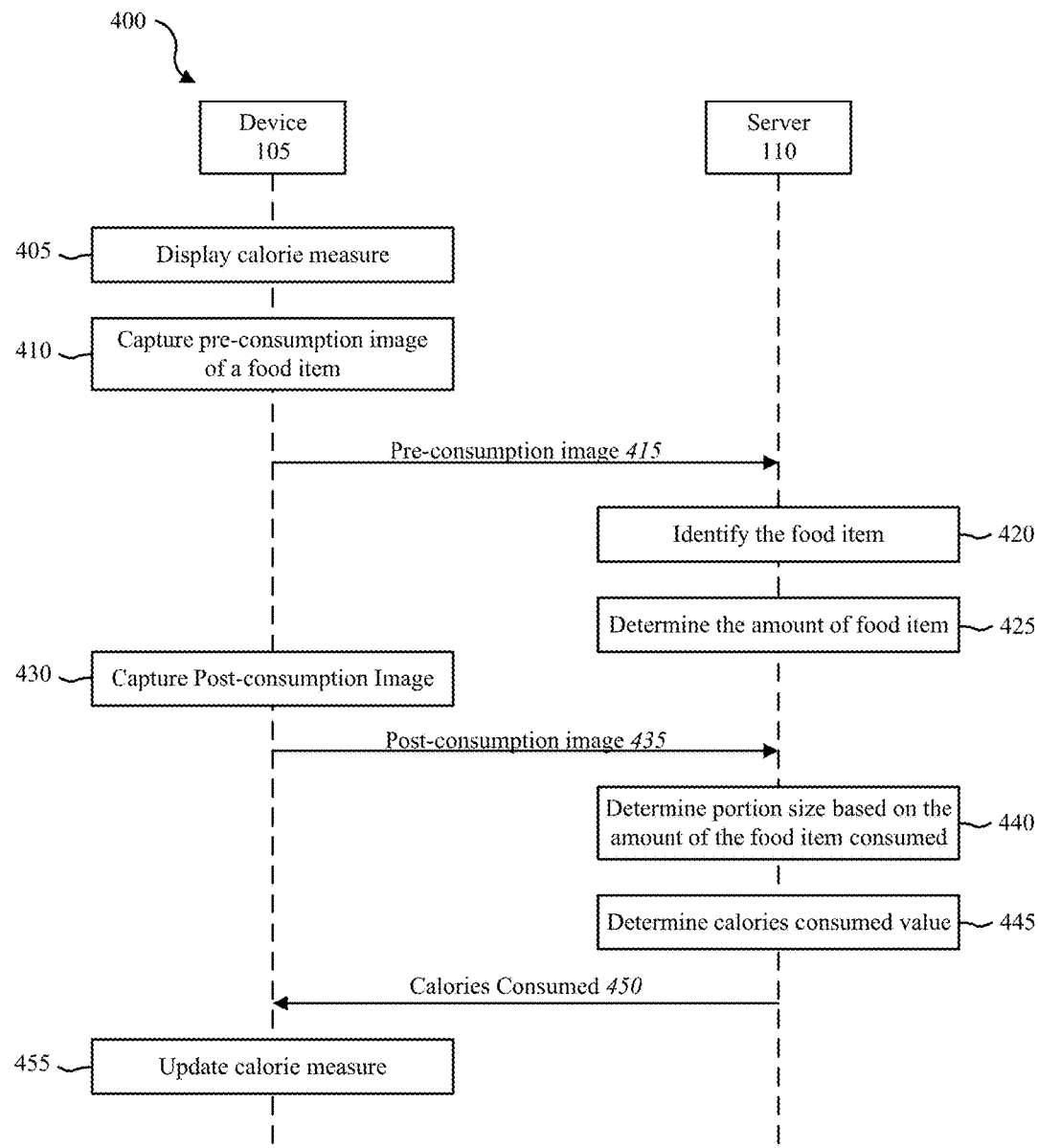
FIG. 4 illustrates one example of the message flow between the device and the server for updating a calorie measure.

FIG. 4 illustrates one example 400 of the message flow between the device 105 and the server 110 for updating a calorie measure. At step 405, the device 105 may display a calorie measure. For example, the device 105 may display the calorie measure in display 130 that is in the field of view of the consumer. In one example, the calorie measure may represent the number of calories that the consumer has already consumed for the day. At step 410, the device 105 may capture (using the camera 130, for example) a pre-consumption image of a food item. In one example, the pre-consumption image of the food item may be captured automatically when the device 105 detects that a consumption event is about to happen. At step 415, the pre-consumption image may be transmitted to the server 110.

At block 420, the server 110 may identify the food item 420. For example, the server 110 may automatically identify the food item based on the visual properties of the food item. Alternatively, the food item may be identified by a human analyst. At block 425, the amount of food item may be determined.

At block 430, the device 105 may capture a post-consumption image. In some cases, the post-consumption image may include the left over portion of the food item. In other case, the food item may be completely eaten so that the post-consumption image may not include any leftover portions of the food item. At block 435, the device 105 may transmit the post-consumption image to the server 110.

At block 440, the server 110 may determine a portion size based on the amount of the food item that was consumed. For example, the difference between the amount of the food item in the pre-consumption image and the amount of the food item in the post-consumption image may correspond with the size of the portion that was consumed. At block 445, the server 110 may determined a calories consumed valued based on the determined portion size of the food item that was consumed. At block 450, the server 110 may transmit the calories consumed value to the device 105.

Upon receiving the calories consumed value, the device 105 may update the calorie measure 455. This may allow for the calorie measure to be dynamically updated without interaction from the consumer.

Figure 5:
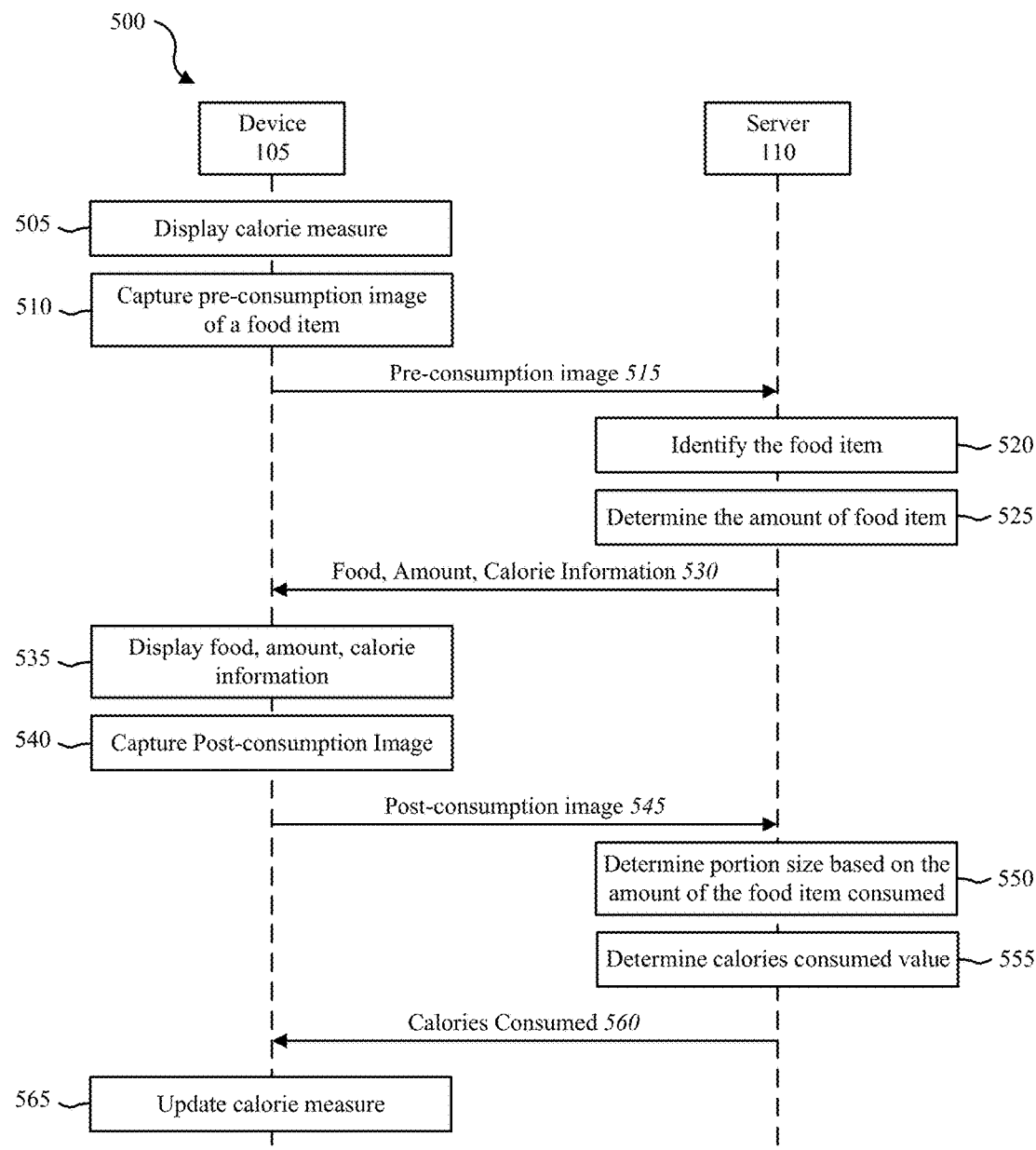
FIG. 5 illustrates another example of the message flow between the device and the server for updating a calorie measure.

FIG. 5 illustrates another example 500 of the message flow between the device 105 and the server 110 for updating a calorie measure. At block 505, the device 105 may display a calorie measure (on the display 135, for example). At block 510, the device 105 may capture a pre-consumption image of a food item. At block 515, the device 105 may transmit the pre-consumption image to the server 110.

At block 520, the server 110 may identify the food item. At block 525, the server 110 may determine the amount of the food item. For example, the server 110 may determine that a bowl of ice cream includes two and half servings of rocky road ice cream. In some cases, the server 110 may determine the calorie information for the food item (e.g., total calories for the two and half servings of rocky road ice cream). At block 530, the server 110 may transmit the information (e.g., food, amount, and/or calorie information, etc.) to the device 105.

At block 535, the device 105 may display at least a portion of the information received from the server 110. For example, the device 105 may display the identified food, the determined amount of the food, and/or the calorie information for the amount of the food item. At block 540, the device

105 may capture a post-consumption image (of the remaining food item or illustrating that there is no remaining amount of the food item, for example). At block 545, the device 105 may transmit the post-consumption image to the server 110.

At block 550, the server 110 may determine a portion size based on the amount of the food item consumed. At block 555, the server 110 may determine a calories consumed value. At block 560, the server 110 may transmit the calories consumed value to the device 105. Upon receiving the calories consumed value, the device 105 may, at block 565, update the calorie measure (to reflect the number of calories consumed, for example).

Figure 6:
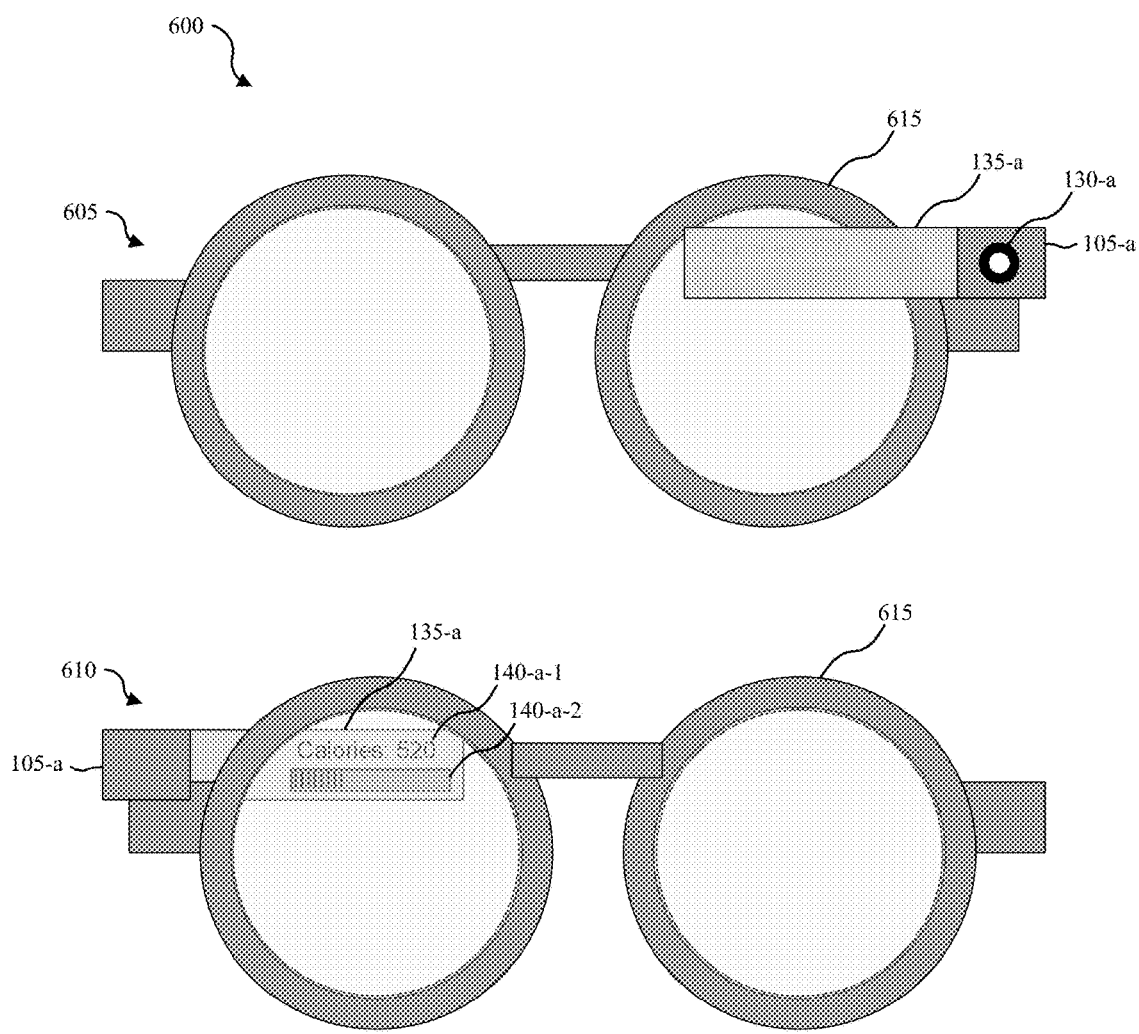
FIG. 6 illustrates one example of a device for implementing the systems and methods described herein.

FIG. 6 illustrates one example 600 of a device 105-*a* for implementing the systems and methods described herein. The device 105-*a* may be an example, the of the devices 105 illustrated in FIGS. 1, 4, and/or 5. As illustrated in FIG. 6, the device 105-*a* may include a camera 130-*a* and a display 135-*a*. In one example, the device 105-*a* may be coupled to a pair of glasses 615. In some cases, the combination of the device 105-*a* and the glasses 615 may be referred to as smart glasses. It is understood that the device 105-*a* may be integrated into the glasses 615 in a variety or ways. Similarly, the device 105-*a* may be integrated into a variety of other wearable products (e.g., contacts, hats, visors, headbands, watches, etc.). For example, the device 105-*a* may be integrated in a way such that the display 135-*a* may be in the field of view (e.g., peripheral field of vision) of the user that is using the device 105-*a*. In FIG. 6, both a front view 605 (e.g., from the outside looking in) and a back view 610 (e.g., from the inside looking out) are shown.

As is shown in FIG. 6, the camera 130-*a* may face outward (so that is captures at least a portion of the field of view of the user, for example). The camera 130-*a* may be an example of the camera 130 illustrated in FIG. 1. As is shown in FIG. 6, the display 135-*a* may face inward (so that the display is within the field of view and viewable by the user who is looking out, for example). The display 135-*a* may be an example of the display 135 illustrated in FIG. 1. As illustrated in FIG. 6, the display 135-*a* may display the calorie measure of the user (e.g., the number of calories the user has consumed). In some cases, the calorie measure may be shown in various formats (e.g., additionally or alternatively). For example, the display 135-*a* may display a first calorie measure 140-*a*-1 in a textual format and/or may display a second calorie measure 140-*a*-2 in a graphical format. It is understood that the display 135-*a* may display a variety of information in addition to or in place of the calorie measure.

Figure 7:
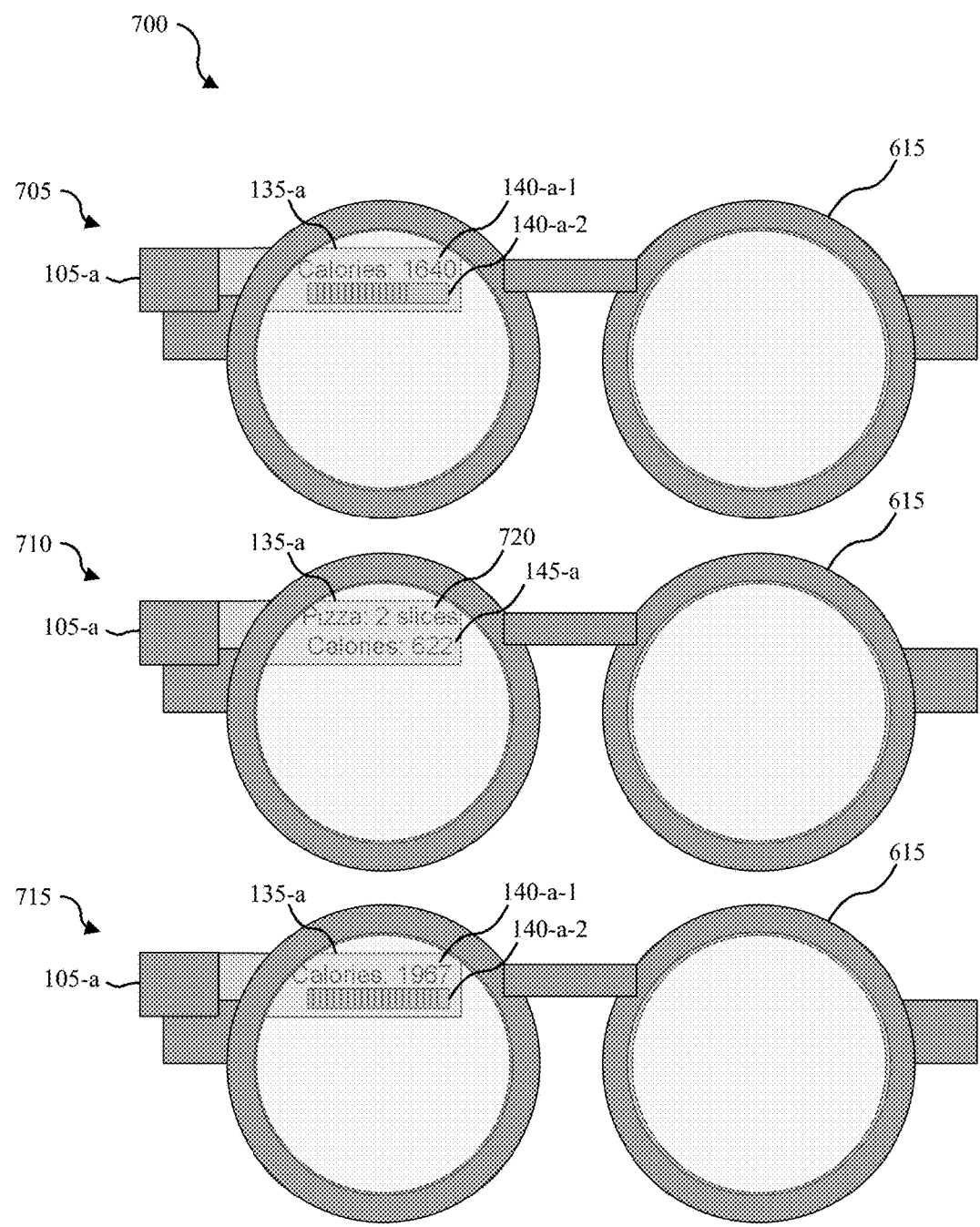
FIG. 7 illustrates an example of how the display may change as a result of a consumption event.

FIG. 7 illustrates an example 700 of how the display 135-*a* may change as a result of a consumption event. As illustrated in FIG. 7, the display 135 is shown at a first time instance 705, a second time instance 710, and a third time instance 715. In one example, the various time instances may correspond with the message flow illustrated in FIG. 5. At the first time instance 705, one or more calorie measures 140-*a*-1, 140-*a*-2 may be displayed on the display 135-*a*. For example, the calorie measure 140 may be displayed in such a way that the calorie measure 140 is in the field of view (e.g., peripheral view) of the consumer that is wearing the device 105-*a* (e.g., glasses 615). In some cases, this may allow for the consumer to be constantly reminded of their calorie consumption status (for the day, for example).

In one example, the device 105-*a* may determine that a consumption event is possible. For example, the device 105-*a* may determine that a consumption event is possible when a food item is in the field of view of the consumer (which may be determined based on an image captured by a camera of the device 105-*a*, for example). In one example, the image (e.g., pre-consumption image) may depict two slices of pizza on the consumer's plate. In another example, the image may depict the two slices of pizza folded together in the consumers hand on the way to the consumer's mouth. At the second time instance 710, the food item (e.g., pizza) and the amount (e.g., two slices) 720 may be displayed. The calorie information 145-*a* for the food item and the portion amount may be displayed. This may provide instant feedback for the consumer as to the amount of calories that they may potentially consume. In some cases, this information may inform the consumer so that they may make better consumption decisions (to not eat or eat only a portion of the food item, for example).

In one example, the device 105-*a* may determine that the consumption event has ended. For example, the device 105-*a* may determine that the consumer has consumed all the food, has finished consuming although some portion of the food item is remaining, or that the consumer has chosen not to consume the food item (based on a post-consumption image, for example). In this example, the device 105-*a* may determine that 100% of the first slice of pizza was consumed and that 5% (a bite, for example) of the second slice of pizza was consumed. Accordingly, the display 135-*a* may display an updated calorie measure 140-*a*-1, 140-*a*-2 of 1967 (e.g., 311 calories for the first slice and 16 calories for the portion of the second slice of pizza that was consumed). As illustrated, the first calorie measure 140-*a*-1 may be a numerical representation of the calories consumed and the second calorie measure 140-*a*-2 may be a graphical representation of the calories consumed with respect to a predefined goal (2000 calories, for example). As described herein, the consumer may have accurate calorie consumption data and instant feedback, which may help the consumer to make wise consumption decisions.

Figure 8:
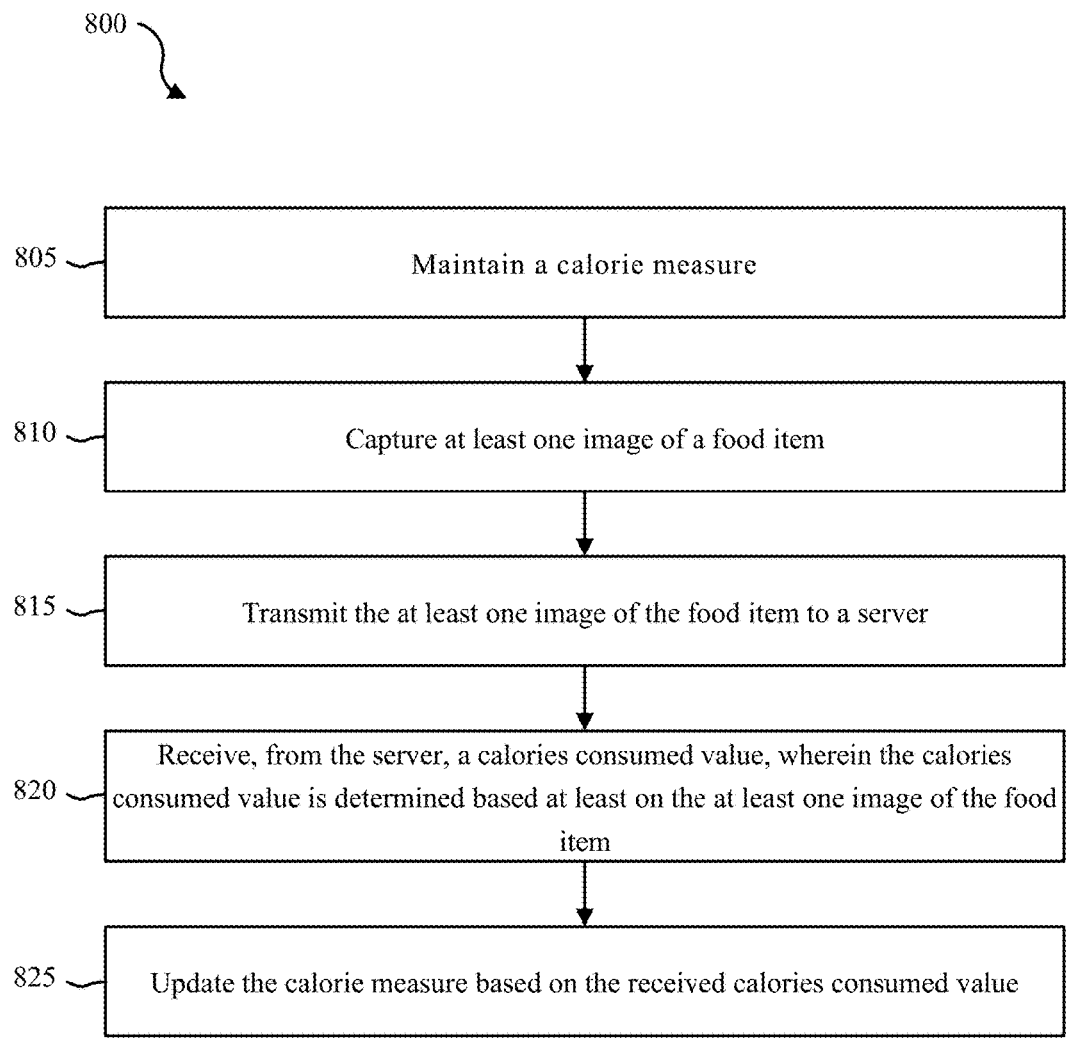
FIG. 8, is a flow diagram illustrating one embodiment of a method for measuring calories using various embodiments of the systems and/or devices described herein.

FIG. 8, is a flow diagram illustrating one embodiment of a method 800 for measuring calories using various embodiments of the systems and/or devices described herein. In one configuration, the method 800 may be implemented by a device such as device 105 illustrated in FIG. 1, 4, 5, 6, or 7. In particular, the method 800 may be implemented by the calorie capture module 125 of FIG. 1 or 2.

At block 805, a calorie measure may be maintained. For example, the calorie measure may be maintained in storage. In another example, the calorie measure may be maintained for so that it may be displayed on a display. At block 810, at least one image of a food item may be captured. At block 815, the at least one image of the food item may be transmitted to a server. At block 820, a calories consumed value may be received from the server. The calories consumed value may be determined based at least in part on the at least one image of the food item. At block 825, the calorie measure may be updated based on the received calories consumed value.

Thus, the method 800 may provide accurate and instantaneous calorie tracking without user interaction. It should be noted that the method 800 is just one implementation and that the operations of the method 800 may be rearranged or otherwise modified such that other implementations are possible.

Figure 9:
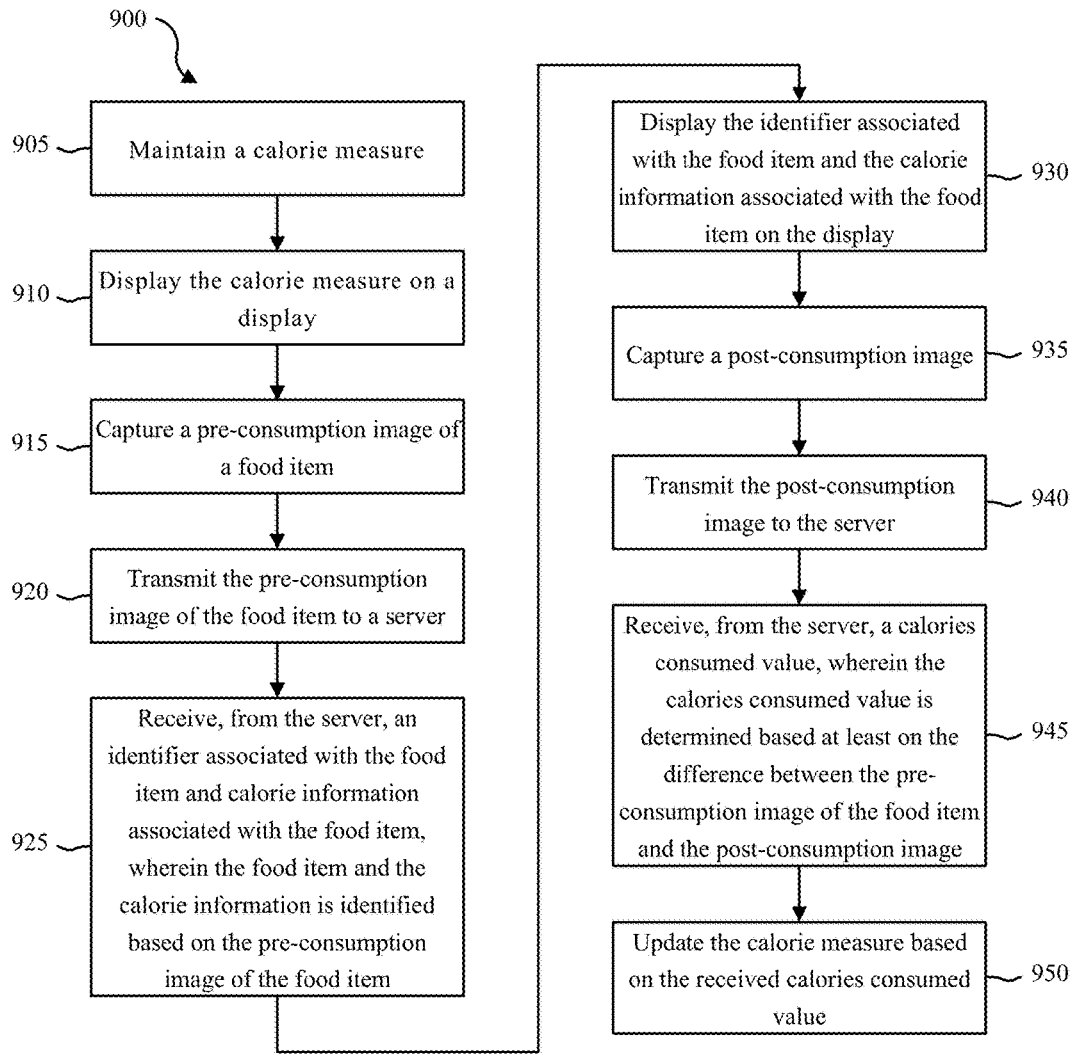
FIG. 9, is a flow diagram illustrating another embodiment of a method for measuring calories using various embodiments of the systems and/or devices described herein.

FIG. 9, is a flow diagram illustrating another embodiment of a method 900 for measuring calories using various embodiments of the systems and/or devices described herein. In one configuration, the method 900 may be implemented by a device such as device 105 illustrated in FIG. 1, 4, 5, 6, or 7. In particular, the method 900 may be implemented by the calorie capture module 125 of FIG. 1 or 2.

At block 905, a calorie measure may be maintained. At block 910, the calorie measure may be displayed on a display. At block 915, a pre-consumption image of a food item may be captured. In one example, the pre-consumption image of the food item may be captured automatically (allowing for automated calorie tracking without consumer interaction, for example). At block 920, the pre-consumption image of the food item may be transmitted to a server. At block 925, an identifier associated with the food item and calorie information associated with the food item may be received from the server. The food item and the calorie information may be identified based on the pre-consumption image of the food item. In some cases, the calorie information for the food item may include amount and/or portion information for the food item.

At block 930, the identifier associated with the food item and the calorie information associated with the food item may be displayed on the display. In one example, this may provide instant feedback to the consumer regarding a possible consumption event. At block 935, a post-consumption image may be captured. At block 940, the post-consumption image may be transmitted to the server. At block 945, a calories consumed value may be received from the server. The calories consumed value may be determined based at least in part on the difference (in amount of the food item, for example) between the pre-consumption image of the food item and the post-consumption image. At block 950, the calorie measure may be updated based on the received calories consumed value.

Thus, the method 900 may provide accurate and instantaneous calorie tracking and instantaneous feedback without user interaction. It should be noted that the method 900 is just one implementation and that the operations of the method 900 may be rearranged or otherwise modified such that other implementations are possible.

Figure 10:
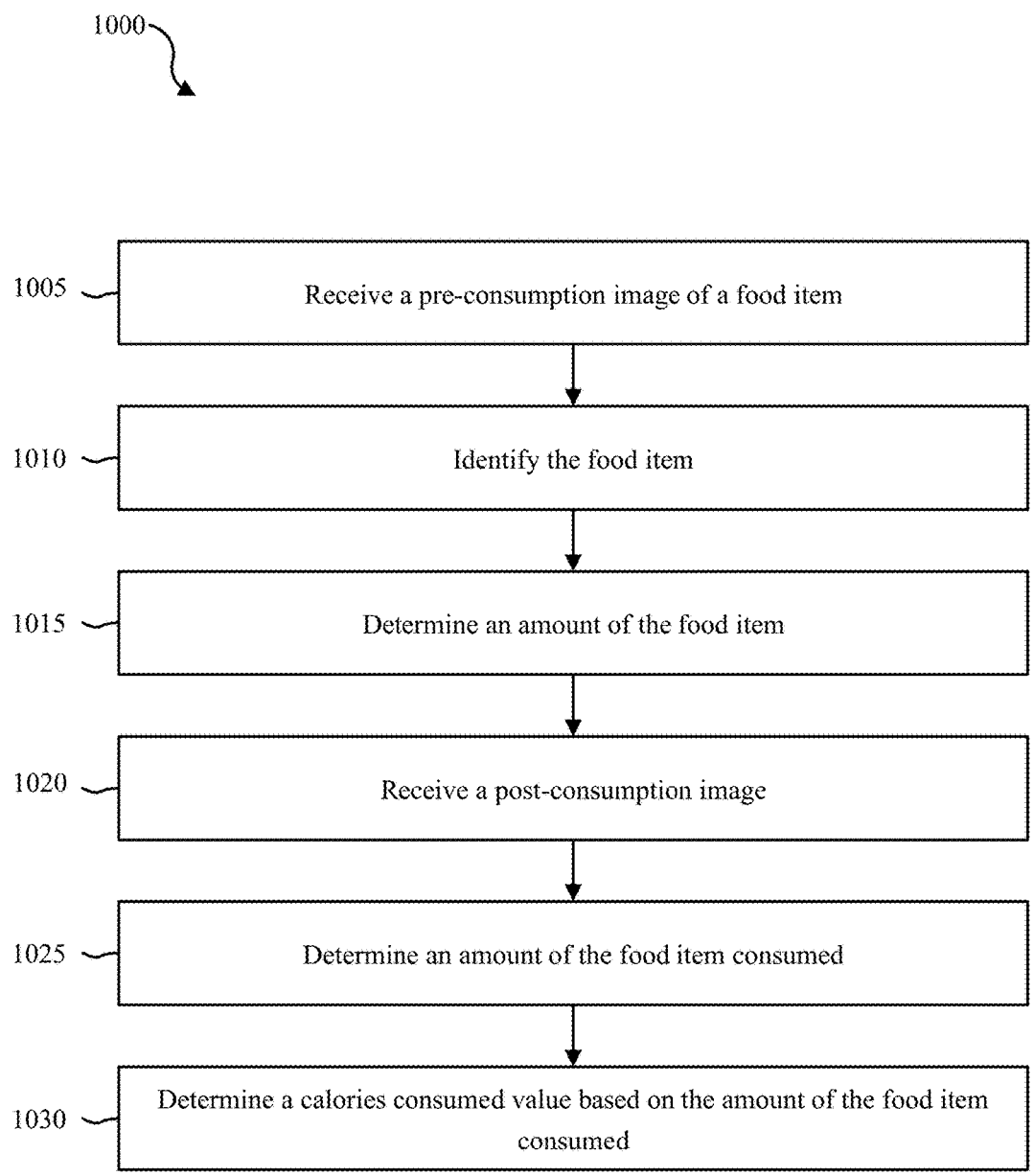
FIG. 10, is a flow diagram illustrating one embodiment of a method for measuring calorie consumption using various embodiments of the systems and/or devices described herein.

FIG. 10, is a flow diagram illustrating one embodiment of a method 800 for measuring calorie consumption using various embodiments of the systems and/or devices described herein. In one configuration, the method 1000 may be implemented by a device such as server 110 illustrated in FIG. 1, 4, or 5. In particular, the method 1000 may be implemented by the calorie measurement module 150 of FIG. 1 or 3.

At block 1005, a pre-consumption image of a food item may be received. At block 1010, the food item may be identified. For example, the food item may be identified using image processing and image analysis techniques. In another example, the food item may be identified by a user (e.g., an analyst) that is viewing the pre-consumption image of the food item. At block 1015, an amount of the food item may be determined. At block 1020, a post-consumption image may be received. At block 1025, an amount of the food item consumed may be determined. For example, the amount of the food item consumed may be determined based on the difference in amount of the food item present between the pre-consumption image and the post-consumption image. At block 1030, a calories consumed value may be determined based on the amount of the food item consumed.

Thus, the method 1000 may provide accurate and instantaneous determination of calories consumed based on the difference between the pre-consumption image and the post-consumption image. It should be noted that the method 1000 is just one implementation and that the operations of the method 1000 may be rearranged or otherwise modified such that other implementations are possible.

Figure 11:
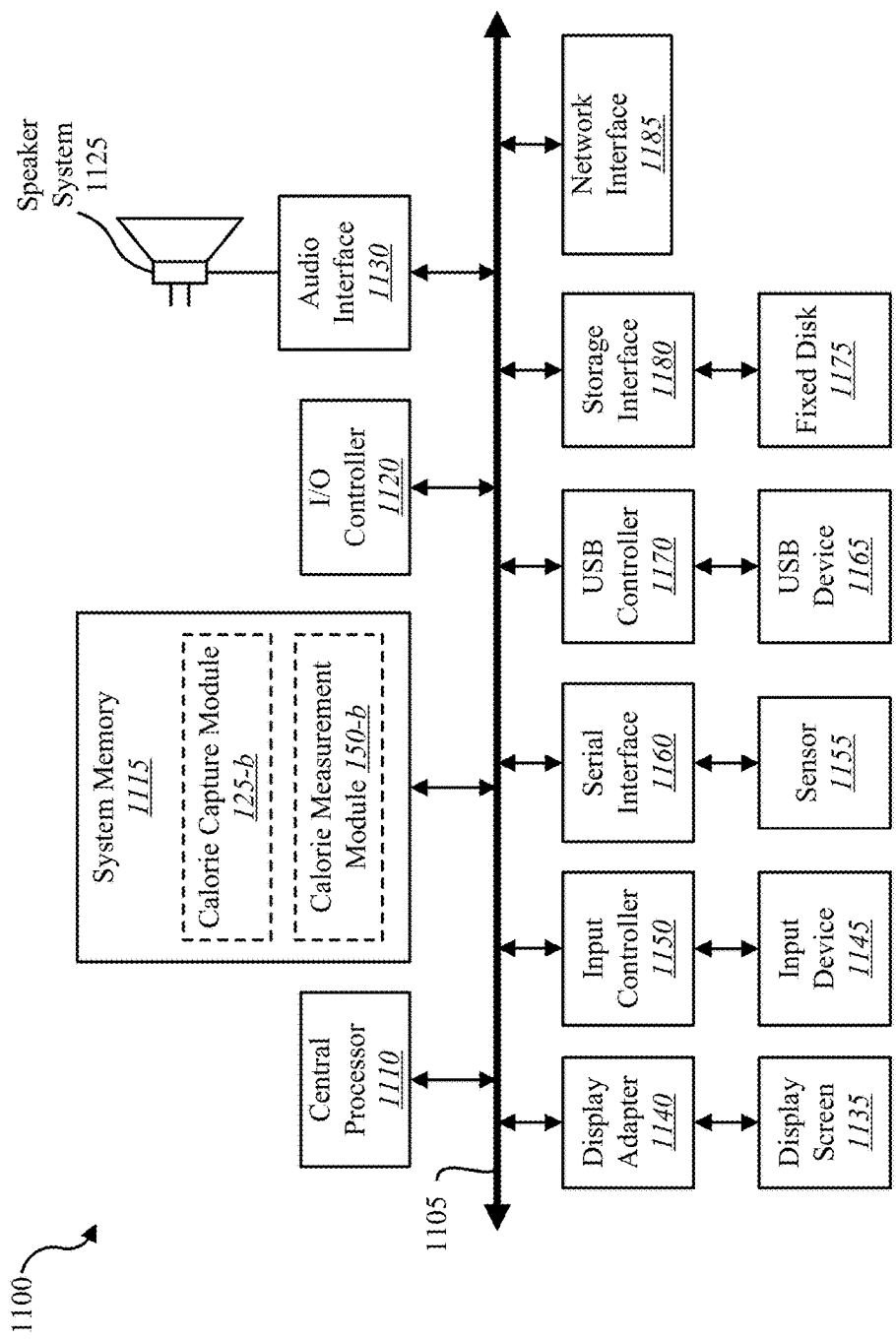
FIG. 11 depicts a block diagram of a computer system suitable for implementing the present systems and methods.

FIG. 11 depicts a block diagram of a computer system 1100 suitable for implementing the present systems and methods. Computer system 1100 includes a bus 1105 which interconnects major subsystems of computer system 1100, such as a central processor 1110, a system memory 1115 (typically RAM, but which may also include ROM, flash RAM, or the like), an input/output controller 1120, an external audio device, such as a speaker system 1125 via an audio output interface 1130, an external device, such as a display screen 1135 via display adapter 1140, an input device 1145 (e.g., keyboard, touchpad, touch screen, voice recognition module, etc.) (interfaced with an input controller 1150), multiple USB devices 1165 (interfaced with a USB controller 1170), and a storage interface 1180. Also included are a sensor 1155 (motion sensor or other motion capture device) connected to bus 1105 through serial interface 1160 and a network interface 1185 (coupled directly to bus 1105).

Bus 1105 allows data communication between central processor 1110 and system memory 1115, which may include read-only memory (ROM) or flash memory (neither shown), and random access memory (RAM) (not shown), as previously noted. The RAM is generally the main memory into which the operating system and application programs are loaded. The ROM or flash memory can contain, among other code, the Basic Input-Output system (BIOS) which controls basic hardware operation such as the interaction with peripheral components or devices. For example, the calorie capture module 125-b and/or the calorie measurement module 150-b to implement the present systems and methods may be stored within the system memory 115. Applications resident with computer system 1100 are generally stored on and accessed via a non-transitory computer readable medium, such as a hard disk drive (e.g., fixed disk 1175) or other storage medium. Additionally, applications can be in the form of electronic signals modulated in accordance with the application and data communication technology when accessed via network interface 1185.

Storage interface 1180, as with the other storage interfaces of computer system 1100, can connect to a standard computer readable medium for storage and/or retrieval of information, such as a fixed disk drive 1175. Fixed disk drive 1175 may be a part of computer system 1100 or may be separate and accessed through other interface systems. Network interface 1185 may provide a direct connection to a remote server via a direct network link to the Internet via a POP (point of presence). Network interface 1185 may provide such connection using wireless techniques, including digital cellular telephone connection, Cellular Digital Packet Data (CDPD) connection, digital satellite data connection, or the like.

Many other devices or subsystems (not shown) may be connected in a similar manner (e.g., document scanners, digital cameras, and so on). Conversely, all of the devices shown in FIG. 11 need not be present to practice the present systems and methods. The devices and subsystems can be interconnected in different ways from that shown in FIG. 11. The operation of a computer system such as that shown in FIG. 11 is readily known in the art and is not discussed in detail in this application. Code to implement the present disclosure can be stored in a non-transitory computer-readable medium such as one or more of system memory 1115 or fixed disk 1175. The operating system provided on computer system 1100 may be iOS®, MS-DOS®, MS-WINDOWS®, OS/2®, UNIX®, LINUX®, or another known operating system.

Moreover, regarding the signals described herein, those skilled in the art will recognize that a signal can be directly transmitted from a first block to a second block, or a signal can be modified (e.g., amplified, attenuated, delayed, latched, buffered, inverted, filtered, or otherwise modified) between the blocks. Although the signals of the above described embodiment are characterized as transmitted from one block to the next, other embodiments of the present systems and methods may include modified signals in place of such directly transmitted signals as long as the informational and/or functional aspect of the signal is transmitted between blocks. To some extent, a signal input at a second block can be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered exemplary in nature since many other architectures may be implemented to achieve the same functionality.

The process parameters and sequence of steps described and/or illustrated herein are given by way of example only and may be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

Furthermore, while various embodiments have been described and/or illustrated herein in the context of fully functional computing systems, one or more of these exemplary embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the exemplary embodiments disclosed herein.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present systems and methods and their practical applications, to thereby enable others skilled in the art to best utilize the present systems and methods and various embodiments with various modifications as may be suited to the particular use contemplated.

Unless otherwise noted, the terms "a" or "an," as used in the specification and claims, are to be construed as meaning "at least one of" In addition, for ease of use, the words "including" and "having," as used in the specification and claims, are interchangeable with and have the same meaning as the word "comprising." In addition, the term "based on" as used in the specification and the claims is to be construed as meaning "based at least upon."

What is claimed is:

1. A computer-implemented method for measuring calorie input, comprising:
   receiving a pre-consumption image of a food item;
   analyzing the pre-consumption image of the food item to determine an amount of the food item;
   receiving a post-consumption image of the food item;
   determining a consumption amount of the food item based at least in part on the pre-consumption image and the post-consumption image; and
   determining a calories consumed value based at least in part on the consumption amount of the food item.

2. The method of claim 1, further comprising:
   identifying the food item based at least in part on the pre-consumption image, or the post-consumption image, or both.

3. The method of claim 2, further comprising:
   determining a characteristic of the food item based at least in part on the pre-consumption image, or the post-consumption image, or both using at least one image processing algorithm,
   wherein the characteristic comprises a size of the food item, a color of the food item, a shape of the food item, a position of the food item in the pre-consumption image or the post-consumption image, a texture of the food item, or any combination thereof.

4. The method of claim 3, further comprising:
   determining portion information associated with the identified food item based at least in part on the determined characteristic of the food item.

5. The method of claim 3, further comprising:
   determining calorie information associated with the identified food item based at least in part on the determined characteristic of the food item.

6. The method of claim 3, further comprising:
   transmitting, at a first time, the determined characteristic of the food item, portion information of the food item, or calorie information of the food item, or any combination thereof, to a device associated with an individual.

7. The method of claim 6, further comprising:
   transmitting, at a second time, the calories consumed value to the device associated with the individual.

8. The method of claim 7, wherein the first time is different from the second time.

9. The method of claim 3, further comprising:
   identifying portion information associated with the identified food item based at least in part on retrieving, from a database, the portion information associated with the characteristic of the food item; and
   determining calorie information associated with the identified food item based at least in part on the portion information for the identified food item.

10. The method of claim 1, further comprising:
    receiving, from a device associated with an individual, multiple images of a field of view of the device, wherein the multiple images are captured at a periodic time interval; and processing the multiple images using an image processing and object recognition procedure; and identifying the pre-consumption image and the post-consumption image based at least in part on processing the multiple images.

11. The method of claim 10, further comprising:

generating a consumption event summary; and transmitting the consumption event summary to the device associated with the individual, wherein the consumption event summary comprises a list of food items consumed based at least in part on a food item identified from the multiple images, calories consumed value for each food item in the list of food items, a timestamp associated with a consumption period, and a duration of the consumption period.

12. A computing device configured for measuring calorie input, comprising:

a processor;

memory in electronic communication with the processor;

instructions stored in the memory, the instructions being executable by the processor to:

receive a pre-consumption image of a food item;

analyze the pre-consumption image of the food item to determine an amount of the food item;

receive a post-consumption image of the food item;

determine a consumption amount of the food item based at least in part on the pre-consumption image and the post-consumption image; and determine a calories consumed value based at least in part on the consumption amount of the food item.

13. The computing device of claim 12, wherein the instructions are executable by the processor to:

identify the food item based at least in part on the pre-consumption image or the post-consumption image, or both.

14. The computing device of claim 13, wherein the instructions are executable by the processor to:

determine a characteristic of the food item based at least in part on processing the pre-consumption image or the post-consumption image, or both using at least one image processing algorithm, wherein the characteristic comprises a size of the food item, a color of the food item, a shape of the food item, a position of the food item in the pre-consumption image or the post-consumption image, a texture of the food item, or any combination thereof.

15. The computing device of claim 14, wherein the instructions are executable by the processor to:

determine portion information associated with the identified food item based at least in part on the determined characteristic of the food item.

16. The computing device of claim 14, wherein the instructions are executable by the processor to:

determine calorie information associated with the identified food item based at least in part on the determined characteristic of the food item.

17. The computing device of claim 14, wherein the instructions are executable the by the processor to:

transmit, at a first time, the determined characteristic of the food item, portion information of the food item, or calorie information of the food item, or any combination thereof, to a device associated with an individual.

18. The computing device of claim 17, wherein the instructions are executable by the processor to:

transmit, at a second time, the calories consumed value to the device associated with the individual, wherein the first time is different from the second time.

19. The computing device of claim 12, wherein the instructions are executable the by the processor to:

receive, from a device associated with an individual, multiple images of a field of view of the device, wherein the multiple images are captured at a periodic time interval; and process the multiple images using an image processing and object recognition procedure; and identify the pre-consumption image and the post-consumption image based at least in part on processing the multiple images.

20. A computer-program product to measure calorie input, the computer-program product comprising a non-transitory computer-readable medium having instructions thereon, the instructions being executable by a processor to:

receive a pre-consumption image of a food item;

analyze the pre-consumption image of the food item to determine an amount of the food item;

receive a post-consumption image of the food item;

determine a consumption amount of the food item based at least in part on the pre-consumption image and the post-consumption image; and determine a calories consumed value based at least in part on the consumption amount of the food item.

* * * * *